United States Patent [19]
Grafton et al.

[11] Patent Number: 5,895,425
[45] Date of Patent: Apr. 20, 1999

[54] BONE IMPLANT

[75] Inventors: R. Donald Grafton, Naples, Fla.; Eugene M. Wolf, San Francisco, Calif.

[73] Assignee: Arthrex, Inc., Naples, Fla.

[21] Appl. No.: 09/019,828

[22] Filed: Feb. 6, 1998

Related U.S. Application Data

[60] Provisional application No. 60/037,610, Feb. 12, 1997.

[51] Int. Cl.$^6$ .................................................. A61F 2/28
[52] U.S. Cl. ........................ 623/16; 623/13; 623/20; 606/73; 411/412
[58] Field of Search .............................. 623/13, 16, 20; 606/60, 65, 66, 72, 73, 104; 411/394, 395, 412, 413, 411, 415, 421, 426

[56] References Cited

U.S. PATENT DOCUMENTS

| | | | |
|---|---|---|---|
| 4,985,032 | 1/1991 | Goble | 606/96 |
| 5,098,435 | 3/1992 | Stednitz et al. | 606/73 |
| 5,139,499 | 8/1992 | Small et al. | 606/73 |
| 5,266,075 | 11/1993 | Clark et al. | 623/13 |
| 5,350,380 | 9/1994 | Goble et al. | 606/80 |
| 5,354,300 | 10/1994 | Goble et al. | 606/80 |
| 5,393,302 | 2/1995 | Clark et al. | 623/13 |
| 5,397,356 | 3/1995 | Goble et al. | 623/13 |
| 5,423,823 | 6/1995 | Schmieding | 606/80 |
| 5,431,651 | 7/1995 | Goble | 606/73 |
| 5,562,671 | 10/1996 | Goble et al. | 606/73 |
| 5,571,139 | 11/1996 | Jenkins, Jr. | 606/232 |
| 5,601,562 | 2/1997 | Wolf et al. | 606/86 |
| 5,743,912 | 4/1998 | Lahille et al. | 606/73 |

FOREIGN PATENT DOCUMENTS

| 26 44 215 | 4/1978 | Germany | 411/394 |
|---|---|---|---|

*Primary Examiner*—Mickey Yu
*Assistant Examiner*—Francis K. Cuddihy
*Attorney, Agent, or Firm*—Ostrolenk, Faber, Gerb & Soffen, LLP

[57] ABSTRACT

A surgical implant for securing ligament grafts into a joint. The implant has back-biting threads that allow the implant to be advanced into bone by impaction. If necessary, the implant can be removed from the bone by rotation. The implant is used, for example, for knee ligament repair by forming a longitudinal socket in a bone. The socket is intersected by a transverse pin. A flexible strand is drawn with the pin through the bone. A looped portion of the flexible strand is diverted so as to protrude out of the entrance to the longitudinal socket. The ends of the flexible strand remain accessible on either side of the bone. The ligament graft is captured within the strand loop protruding from the entrance to the socket. The strand is retracted into the socket, drawing the graft into the socket by pulling on the accessible ends of the flexible strand. The graft is fixed in the socket using the transverse implant.

8 Claims, 8 Drawing Sheets

BONE IMPLANT

This application claims the benefit of U.S. Provisional Application Ser. No. 60/037,610, filed Feb. 12, 1997.

BACKGROUND OF THE INVENTION

1. Field of the Invention:

The present invention relates to bone implants. More specifically, the invention relates to surgical implants for graft fixation in arthroscopic ligament repair in the knee using semitendinosus and gracilis tendon autografts.

2. Description of the Related Art:

When a ligament or tendon becomes detached from associated bone, surgery usually is required to re-secure the ligament or tendon. Often, a substitute ligament, or graft, is attached to the bone to facilitate re-growth and permanent attachment. Various methods of ligament graft attachment are known, including staples, suture over buttons, and interference screw fixation.

Various problems exist with the known fixation methods. Staples and suture buttons are disadvantageous because they often do not provide fixation sufficient to withstand the normal tensile loads. With suture button fixation, for example, a strand of suture couples the button and the substitute ligament. This strand becomes the "weakest link in the chain," and if the strand breaks, the ligament detaches.

A stronger graft attachment can be obtained by interference screw fixation, whereby an interference screw is used to wedge a graft bone block to the wall of a graft tunnel. See, e.g., U.S. Pat. Nos. 5,211,647, and 5,603,716, incorporated herein by reference.

Although interference screw attachment is more secure than using staples or suture buttons, it is sometimes neither possible nor desirable to provide such fixation, particularly in the femoral tunnel. In revision situations, for example, where a previous reconstruction has been performed, placing a second femoral tunnel close to the previous tunnel may not be indicated.

In other cases, a semitendinosus graft must be used because the previous reconstruction used the mid third patellar tendon. Although a bone-semitendinosus graft-bone construct may be prepared using a workstation as disclosed in U.S. Pat. No. 5,397,357, such a procedure is time consuming, and may be undesirable for other reasons.

A fixation technique which provides strong attachment of a semitendinosus graft in the femoral tunnel, using a transverse pin, is disclosed in U.S. Pat. No. 5,601,562, of common assignment with the present application. The transverse pin is inserted through a loop in a tendon graft. A threaded portion of the pin screws into the bone as the pin is advanced with rotation into the repair site. The technique is disadvantageous, however, because the graft can wrap around the pin as it is rotated. An improved loading technique is the subject of a co-pending U.S. patent application, attorney docket no. P/1493–147, which also claims the benefit of U.S. Provisional Application Ser. No. 60/037,610, filed Feb. 12, 1997.

Various endoscopic techniques and instruments relating to graft fixation are known in the prior art and can be used in the practice of the present invention as it relates to graft repair of knee ligaments, as follows: U.S. Pat. No. 5,320,636 to Schmieding discusses an endoscopic drill guide for graft tunnel location. U.S. Pat. No. Des. 378,780 illustrates a cannulated headed reamer as can be used in femoral socket formation. U.S. Pat. Nos. 5,269,786 and 5,350,383 disclose drill guides for location of bone tunnels.

The need exists for fixation devices that can be installed without rotation, and yet are removable.

SUMMARY OF THE INVENTION

The present invention overcomes the problems of the prior art and fulfills needs such as those noted above by providing a surgical bone implant that can be advanced into bone by impaction, and can be removed from bone by rotation. The implant is useful for various surgical indications, including fixating tendon grafts in a joint using the implant in a transverse, intraosseous application.

The bone implant has a shaft with distal and proximal ends, and a helical thread formed on the shaft, preferably proximally. The thread has a distal face and a proximal face, and a slope of the distal face is significantly greater than a slope of the proximal face, such that the implant can be driven by impaction into a pre-drilled bone site, and removed from the bone site by rotation.

Preferably, the implant is cannulated, for guided insertion over a drill pin, for example. For ease of insertion, the distal portion of the shaft is tapered, and the shaft has a smooth central portion.

An attachment point for a driver is provided to allow subsequent removal of the implant. The driver is rotated, allowing the back-biting threads on the implant to remove the pin.

The thread is may be formed as a continuous, unbroken helix. Alternatively, breaks, gaps, or other features can be provided on the thread as are known to improve insertion, removal, or ingrowth of tissue. The implant can be molded or machined using known techniques, and preferably is made from a single piece of material. The implant can be made of any material, biologically compatible and biologically resorbable materials being preferred.

As applied in the knee, a method of using the implant includes the use of standard techniques to drill a longitudinal tunnel in the tibia. Subsequently, a femoral socket is formed, preferably in the lateral femoral condyle. According to the present invention, forming the socket is preferred to forming a tunnel through the lateral femoral cortex. Advantageously, the diameters of the tibial tunnel and femoral socket are made just large enough to accommodate the graft in a snug fit.

A tunnel hook, mounted on a cross-pin drill guide, is inserted through the tibial tunnel and into the femoral socket. A drill pin directed by the drill guide is drilled through the femur to intersect the femoral socket. The drill pin passes through the capture slot of the tunnel hook.

A hole then is formed in the femur, preferably using a cannulated drill placed over the guide pin, to accommodate a threaded section of the transtibial implant. A channel is formed in the lateral femoral cortex to accommodate the remainder of the implant, preferably using a dilator placed over the guide pin.

Next, a flexible strand, preferably a wire formed of nitinol, is attached to the guide pin and pulled through the femur. Equal lengths of the strand protrude from the medial and lateral sides of the femoral shaft, and are secured to prevent accidental pull-out. The tunnel hook is withdrawn, the strand being captured in the slot of the hook.

The hook is retracted completely, through the femoral socket and out of the tibial tunnel, such that a loop of the flexible strand protrudes from the entrance to the tunnel. Free ends of the strand remain exposed on either side of the femoral shaft.

The graft is passed through the diverted loop of the flexible strand. The loop is retracted into the femoral socket by pulling evenly on the medial and lateral ends of the strand. As a result, the graft is drawn into the socket.

The cannulated implant is placed over the wire and driven into the femur. The implant is formed with back-biting threads. Accordingly, the implant easily can be impact driven into the repair site, and yet can be removed by rotation. The cannulated implant passes over the strand and under the tendon, thus securing the graft in the femoral socket.

Tibial fixation of the graft can be performed by various known methods, including interference screw fixation, which provides the most secure post-operative result; distal fixation with a cancellous screw using a post and washer technique; and a belt buckle staple technique utilizing a pair of ligament staples.

An alternative method of tendon loading is also provided for a closed-loop graft reconstruction. According to the alternative method, a flexible line is joined to one end of the strand. A strand/line loop is formed so as to protrude from the entrance to the tibial tunnel and present the junction between the strand and the line. The strand and the line are dejoined, opening the strand/line loop to accept the graft. The strand and line are rejoined so as to capture the graft, and the procedure continues substantially as set forth above.

Other features and advantages of the present invention will become apparent from the following description of the invention which refers to the accompanying drawings. For example, although the description herein relates to ACL grafts and forming femoral tunnels in the knee, it will become apparent that expanded indications for the inventive method include other joints and replacement of other ligament or tendon structures using various types of graft constructs.

DETAILED DESCRIPTION OF THE PREFERRED EMBODIMENTS

Figure 8:
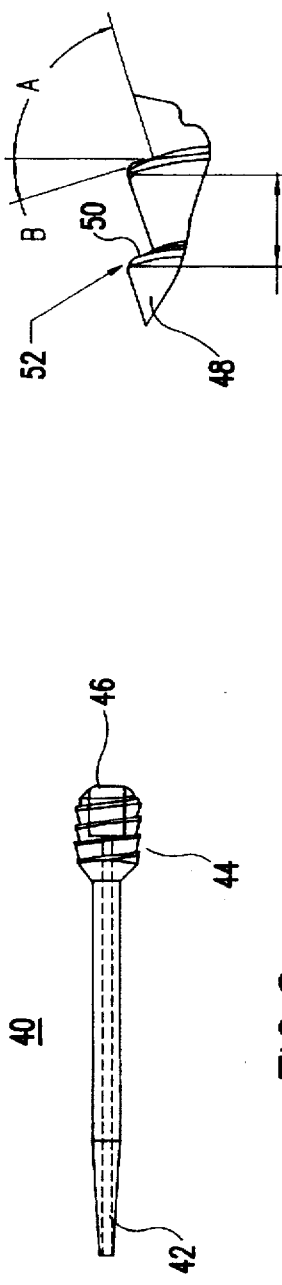
FIG. 8 illustrates a transverse implant having back-biting threads according to the present invention.

The implant of the present invention will be described in conjunction with a surgical method utilizing a preferred embodiment of the implant, which is shown in FIG. 8.

Figure 2:
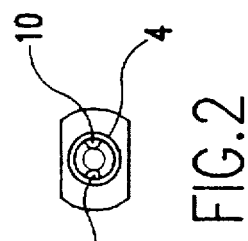
FIG. 2 is a distal end view of the tunnel hook of FIG. 1.
Figure 1:
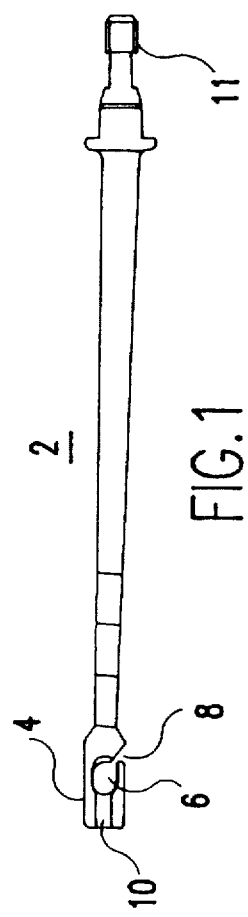
FIG. 1 is an elevation of a tunnel hook according to the present invention.

Referring initially to FIGS. 1 and 2, the present invention involves the use of a slim, longitudinal tunnel hook 2, which includes a shaft having a distal end and a proximal end. The distal end of tunnel hook 2 is provided with a hook 4, having a capture slot 6.

Various features of tunnel hook 2 are provided for ease of use in the inventive procedure of the present invention. The purpose of the following features will become more clear in light of the method described below. Angled opening 8 allows escape of a graft-passing wire from capture slot 6. Channels 10 on either side of hook 4 accommodate portions of the graft-passing wire as it forms a loop through the femoral tunnel. The proximal end of tunnel hook 2 features a mounting flange 11 for engagement with a drill guide.

Figure 3:
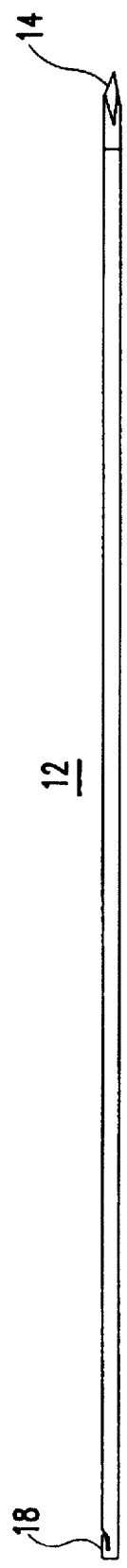
FIG. 3 is an elevation of a drill pin according to the present invention.
Figure 5:
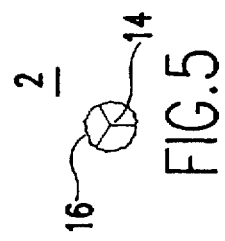
FIG. 5 is a distal end view of the drill pin of FIGS. 3 and 4.
Figure 4:
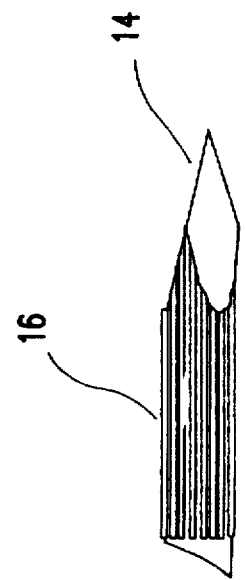
FIG. 4 is an enlarged view of the distal tip of the drill pin of FIG. 3.

Referring to FIGS. 3, 4, and 5, the invention also involves the use of a drill pin 12, which includes an elongated, narrow shaft having a pointed distal end and a proximal end. The distal end of drill pin 12 is provided with a sharp, trocar tip 14 and a fluted drilling region 16 disposed adjacent to and proximal the faces of trocar tip 14. The proximal end of drill pin 12 includes a hook 18 having an angled opening into its capture slot for engaging the graft-passing wire, as described more fully below.

Figure 6:
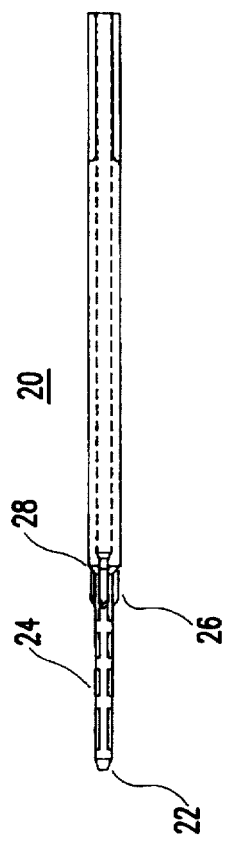
FIG. 6 is an elevation of a tunnel dilator according to the present invention.

Referring to FIG. 6, a tunnel dilator 20 is shown. Tunnel dilator 20 has a tapered distal end and a proximal end. Dilator 20 is cannulated to be received over drill pin 12. The dilator has an initial taper 22 at the distal end for insertion into the bone where the drill pin enters. A cylindrical portion 24 forms a channel in the femur for receiving an implant shaft. An interim fluted portion 26 can be provided alternatively to form a hole for receiving threads of the implant, as described below. A depth stop 28 is formed proximally.

Figure 7:
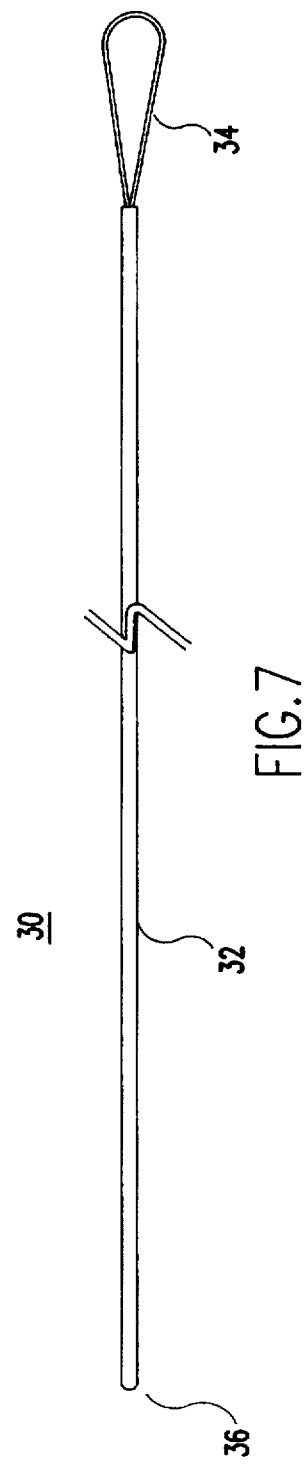
FIG. 7 illustrates a graft-passing wire according to the present invention.

Referring to FIG. 7, a nitinol graft-passing wire 30 is shown. Passing wire 30 includes a flexible portion 32 having a loop 34 formed on the distal end and a rounded proximal end 36.

Figure 9:
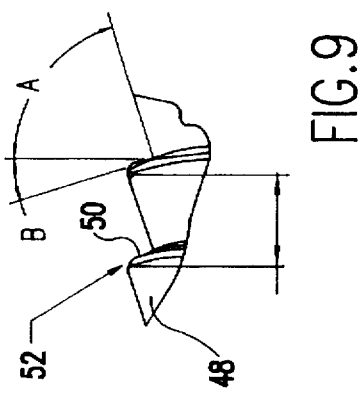
FIG. 9 is an enlarged detail view of the back-biting threads of the transverse implant illustrated in FIG. 8.
Figure 10:
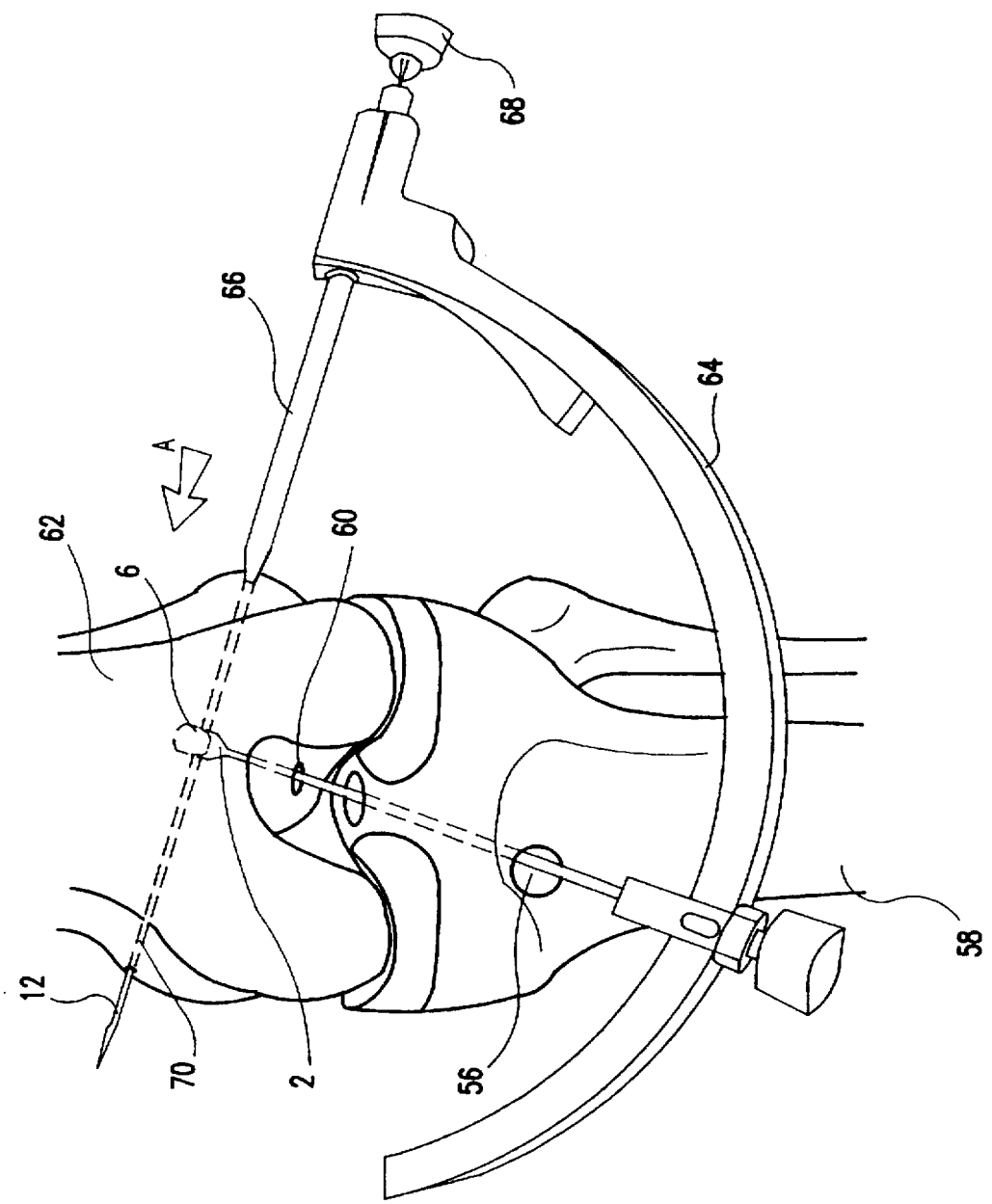
FIG. 10 is a schematic view of a hook and a drill pin mounted on a drill guide and disposed within the femoral socket according to the present invention.

FIGS. 8 and 9 illustrate a transverse implant 40. Implant 40 has a threaded proximal end and a distal end. The implant is cannulated to be received over graft-passing wire 30. The implant has a taper 42 formed toward the distal end. The proximal end includes back-biting, helical threads 44 and a drive socket 46. As shown in detail in FIG. 9, threads 44 have a sloping distal face 48 and a proximal face 50 meeting at a radiused edge 52. Distal face 48 forms an angle A of about 72° with a perpendicular to the central axis of the implant. Proximal face 50 forms an angle B of about 18° with the perpendicular. The implant can be driven by impaction into bone, and then, if necessary, can be subsequently removed by screw rotation as discussed below.

The method of the present invention is described with reference to FIGS. 10 through 16. A longitudinal tibial tunnel 56 is formed using known techniques of drilling up through the tibia 58. Reproducible tunnel placement is achieved using instruments that reference intra-articular anatomical constants. A cannulated drill, received over a guide, is used to drill the tibial tunnel. Depending on the size of the graft, tunnel diameters of 7, 8, 9, and 10 mm are can be used.

Once the tibial tunnel is formed, a cannulated headed reamer is used to form a closed-ended socket 60 in the femur 62. The socket is formed to a minimum depth of about 40 mm to accommodate the insertion depth of tunnel 20 to hook 2. The knee should be placed in 90° of flexion when forming the tibial tunnel and femoral socket.

The tunnel and socket can be modified in various ways using tunnel taps. For example, crenulations formed in the tibial tunnel provide additional friction and helps eliminate unwanted graft rotation during interference screw insertion. A spiral groove formed in the tunnel wall provides additional interference friction of the graft collagen against the compressed cancellous bone in the tunnel. A rasp may be used to create an oval-shaped tunnel and femoral socket to accommodate insertion of four tendon strands.

After the tibial tunnel and femoral socket are complete, tunnel hook 2, fitted onto a C-ring cross-pin drill guide 64, is inserted through tibial tunnel 56 and into femoral socket 60. Tunnel hook 2 will capture within slot 6 the graft-passing wire 12 used in loading the graft tendons into the femoral socket, as described below with respect to FIGS. 12 and 13.

Referring again to FIG. 10, with tunnel hook 2 and drill guide 64 in place, a 2 mm drill pin sleeve 66 is advanced in the direction of arrow A up to the skin proximal to the femoral condyle to indicate an incision site. The drill guide is positioned to allow the pin to pass parallel to the coronal plane, without excessive posterior or anterior divergence. A 2-cm incision is made transversely at this site through the skin and fascia lata, and soft tissue is cleared down to the condyle.

Drill pin sleeve 66 is advanced until it contacts bone. Over-tightening of the drill pin sleeve against the femoral cortex is avoided to prevent the drill pin from deviating and missing capture slot 6 of tunnel hook 2. A depth indicator on the sleeve is used to gauge the length of implant 40 that will be required. With the sleeve in position against the cortical bone, drill pin 12, 2 mm. in diameter, is chucked into a power drill 68, and advanced with rotation through the femur until it exits the skin on the medial side 70. To ensure that the drill pin passes within the capture slot 6 of tunnel hook 2, torque on the drill guide and changes in knee flexion are avoided during drilling.

Figure 11:
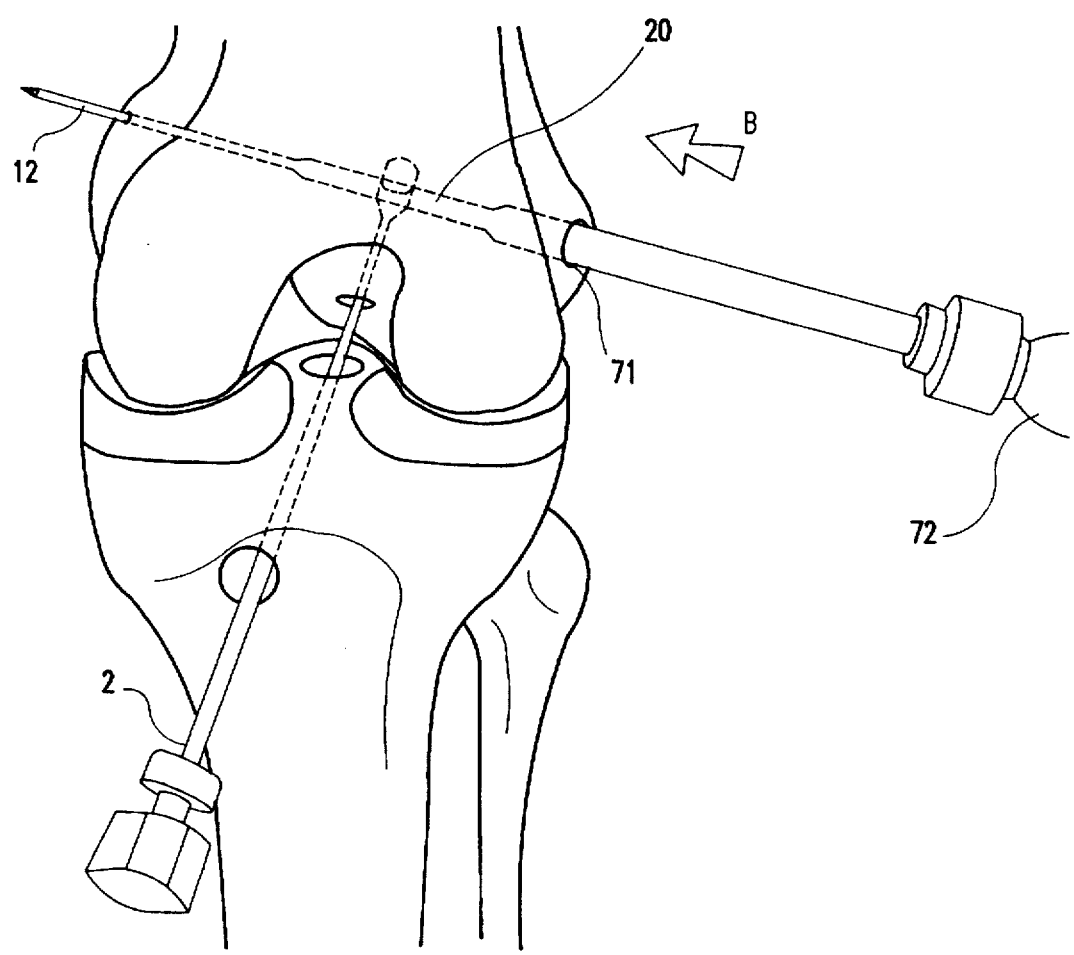
FIG. 11 is a schematic view of a tunnel dilator being used to form a femoral channel for the transverse implant according to the present invention.

Referring to FIG. 11, a cannulated drill is placed over the guide pin to drill a hole 71 to accommodate threaded section 44 of implant 40. The drill is replaced with tunnel dilator 20, which is used to form a channel in the femur for the remainder of implant 40. Tunnel dilator 20 is mounted onto a driver/extractor 72 and driven with a mallet in the direction of arrow B up to the depth stop 28.

Figure 12:
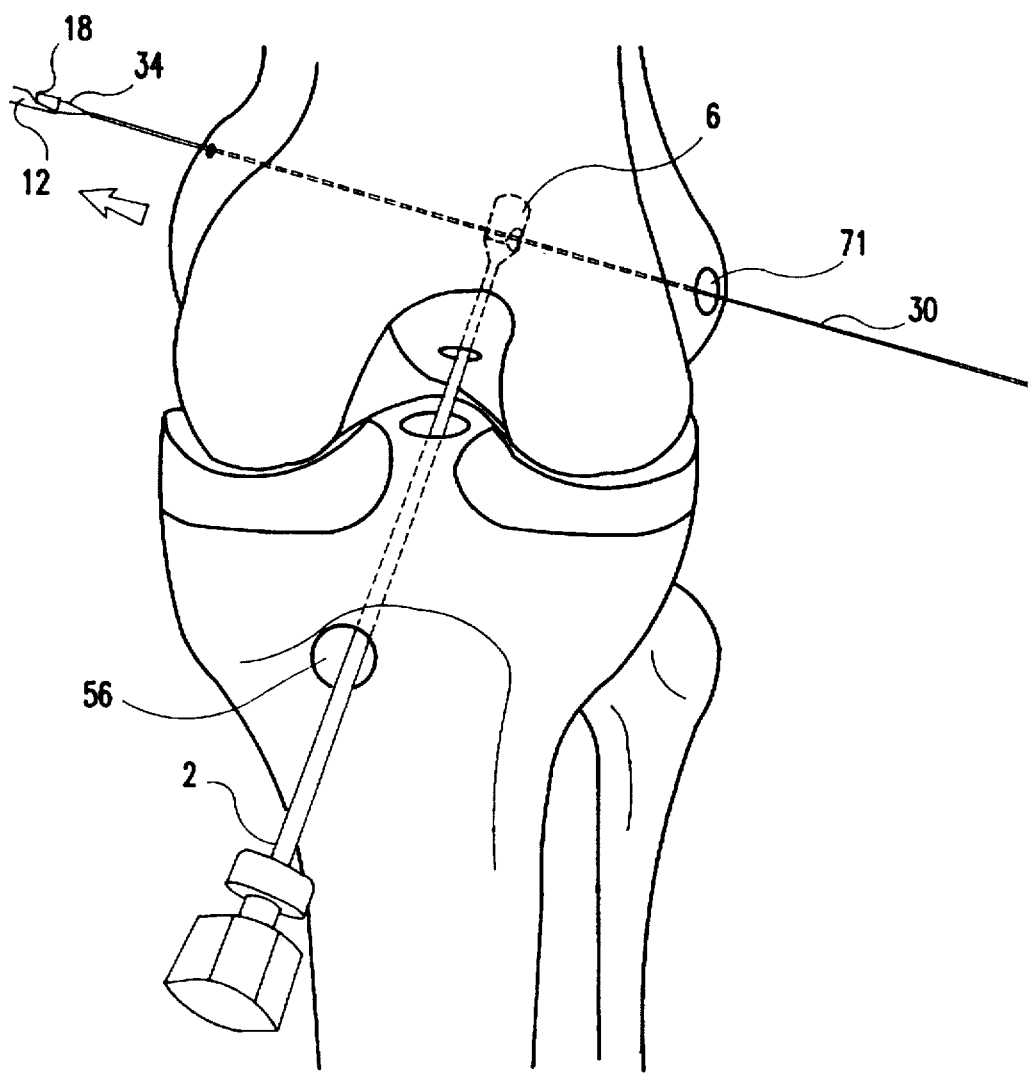
FIG. 12 illustrates a flexible strand attached to the drill pin and being pulled through the femur according to the present invention.

Referring to FIG. 12, once the channel has been formed, loop 34 of nitinol graft-passing wire 30 is hooked onto hook 18 on the proximal end of drill pin 12. By pulling on the drill pin, the graft-passing wire is drawn through the femur until it is positioned with equal lengths at either end protruding from the medial and lateral sides of the femoral shaft. Hemostats 74 are clipped onto the ends of the wire to prevent them from being pulled into the transverse femoral tunnel 70, as shown in FIG. 14.

Figure 13:
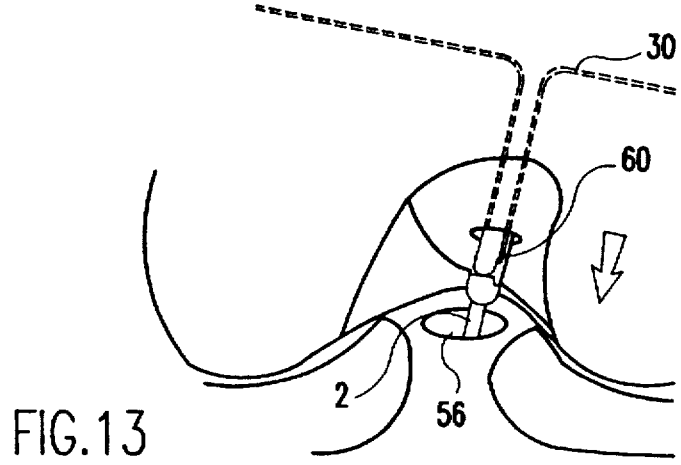
FIG. 13 illustrates a loop of the flexible strand being pulled by the hook and out through the femoral socket according to the present invention.
Figure 14:
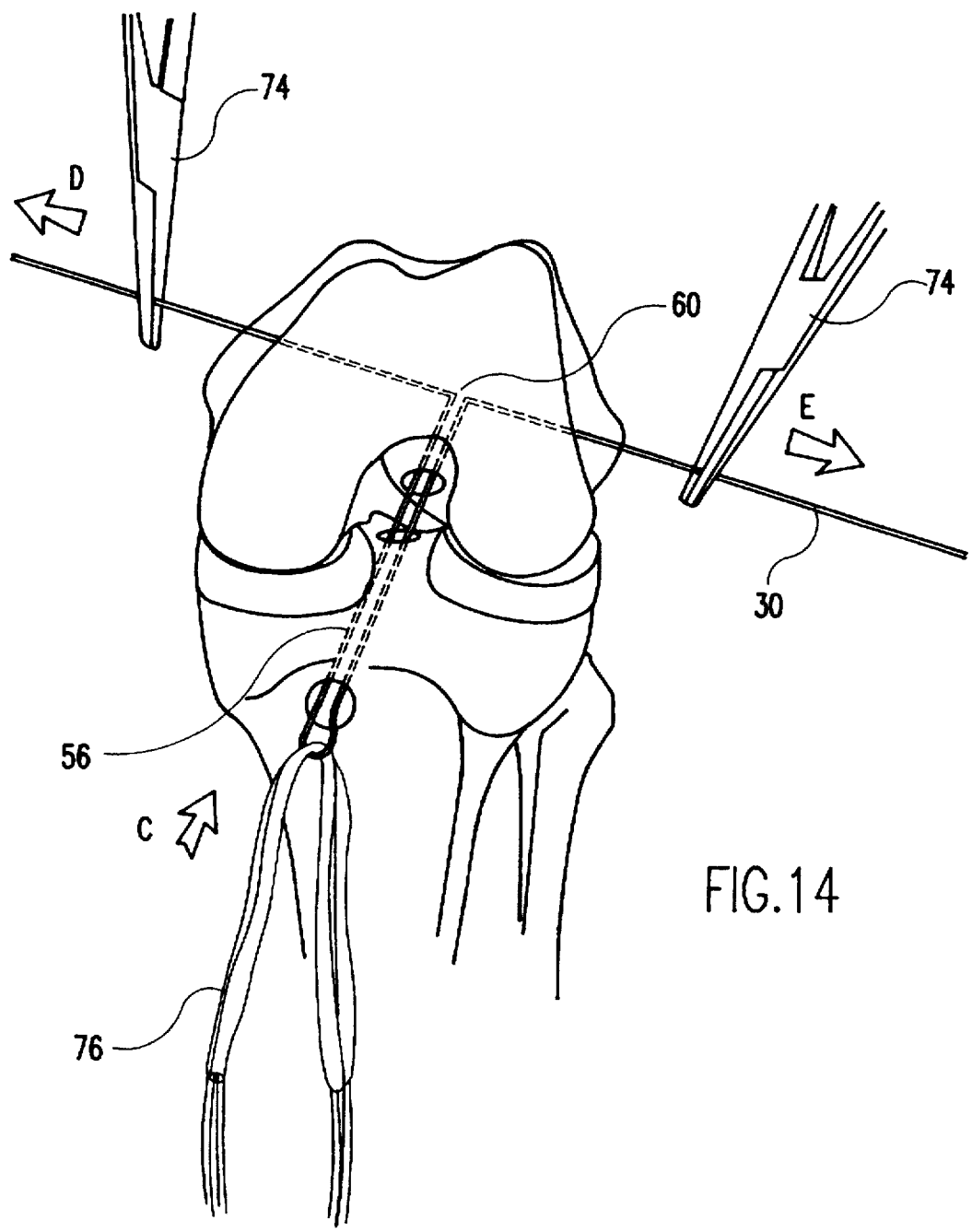
FIG. 14 illustrates the flexible strand loop having been diverted through the tibial tunnel, capturing a ligament graft, and pulling the graft into the tibial tunnel according to the present invention.

Referring to FIGS. 13 and 14, once the graft-passing wire has been drawn through the femur, tunnel hook 2 is retracted from femoral socket 60 and tibial tunnel 56, pulling graft-passing wire 30 with it to form a loop that protrudes from the entrance of tibial tunnel 56 on the anterior tibial cortex. The semitendinosus and gracilis tendons 76 are placed evenly over the wire loop, and the loop containing the tendons is retracted in the direction of arrow C back through the tibial tunnel and into the femoral socket by pulling evenly on the medial and lateral ends of the graft-passing wire, as shown by arrows D and E, respectively. Twisting of the graft during insertion is avoided.

Figure 15:
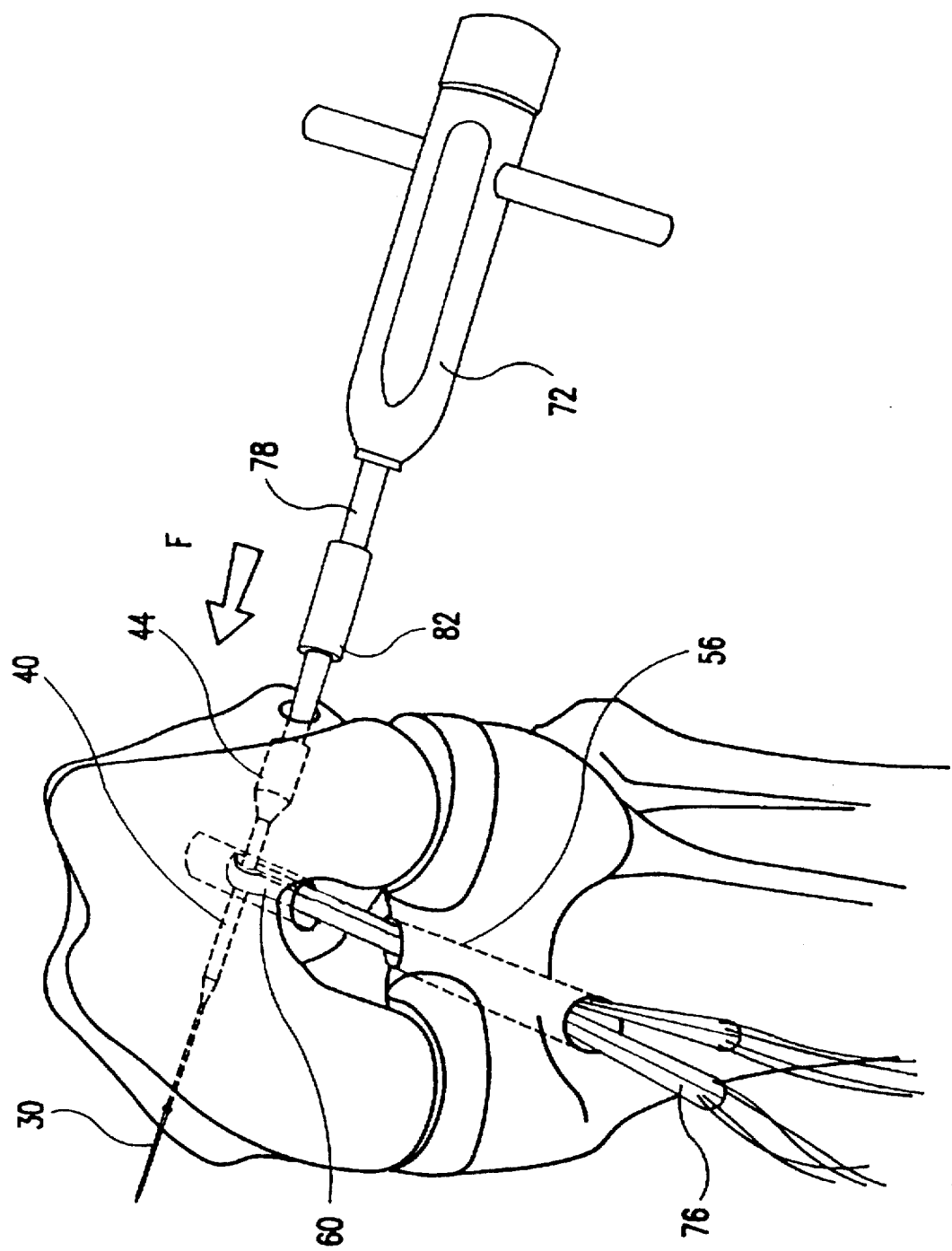
FIG. 15 illustrates the ligament graft, having been loaded through the longitudinal tibial tunnel and into the femoral socket, being fixated using a transverse pin according to the present invention.

Referring to FIG. 15, once the tendons 76 have been drawn completely into femoral socket 60, implant 40 is inserted over the guide wire and advanced by hand until the threaded section 44 contacts the femur. An implant impactor 78 is chucked into driver/extractor 72 and placed over the wire 30. The head of the implant 40 is engaged and a mallet is used to drive the implant into the femur until a depth stop 82 on the driver 78 contacts the cortical bone. Pulling on the tendons 76 is avoided during impaction of the implant 40.

The implant is advanced along the wire in the direction of arrow F. The implant passes under the loop formed in tendons 76, toward the medial side of the femur, to provide cross-pin support of tendons 76. If removal of the implant should become necessary, reverse cutting threads 44 facilitate removal by unscrewing the implant with a 3.5 mm hex head screwdriver.

Figure 16:
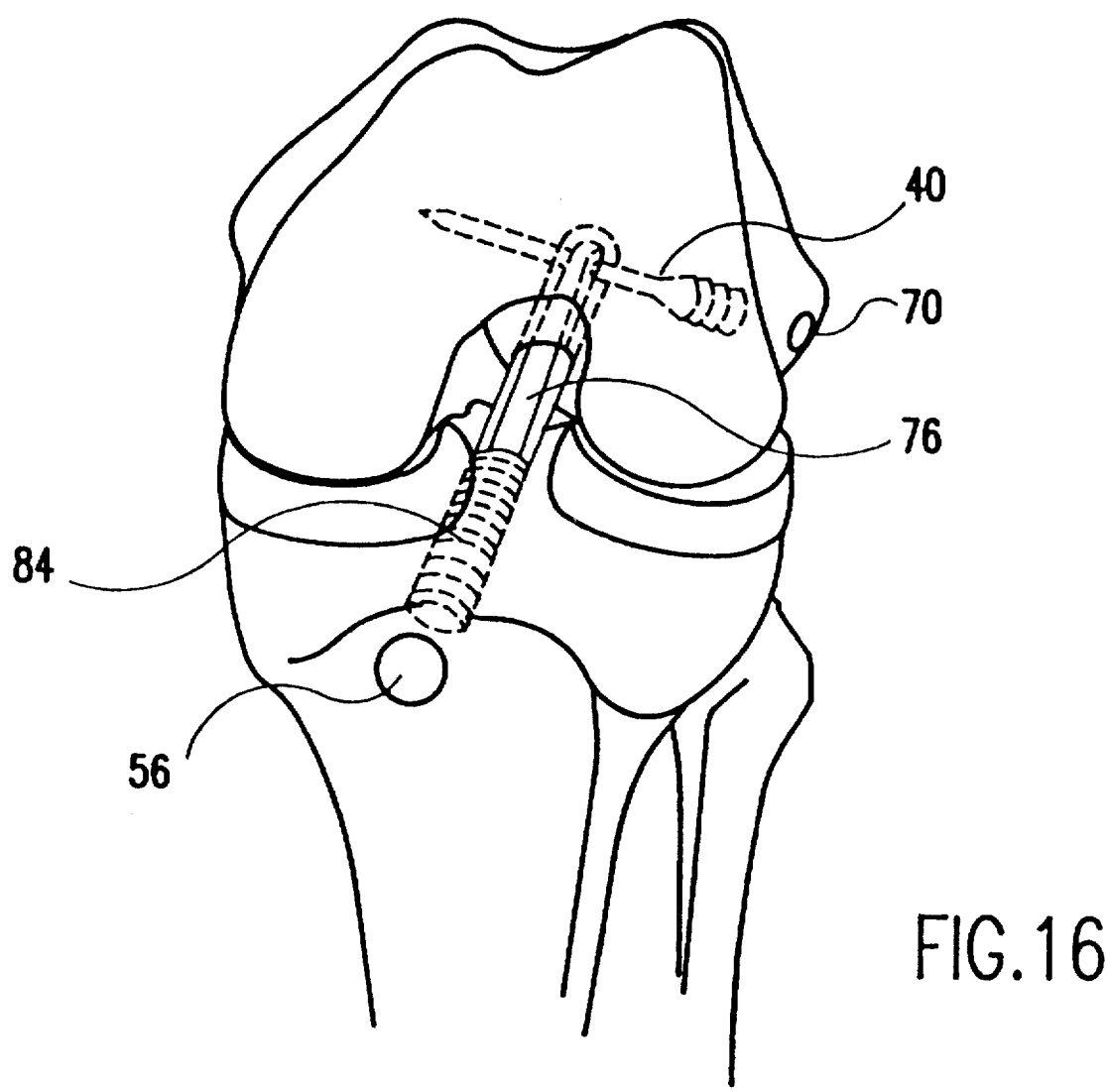
FIG. 16 illustrates a completed tendon graft repair including tibial fixation with an interference screw.

Referring to FIG. 16, the repair is completed by interference screw 84 fixation of graft 76 in tibial tunnel 56. The femoral tunnel is narrow so that tendons 76 fit snugly within tibial tunnel 56 and femoral socket 60, thus avoiding wiping of the tendons along the implant.

Variations, modifications, and other uses of the present invention will become apparent to those skilled in the art, including the following, non-limiting examples: attachment of bone to bone; attachment of soft tissue to bone; non-medical applications.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A bone implant formed of a biologically compatible material, comprising:

a shaft having a distal end, a proximal end, and a central axis, said bone implant having a cannulation disposed along the central axis of the shaft and extending completely through the implant from the distal end to the proximal end, such that said implant is adapted to be advanced over a guide wire into the body of a patient; and a back-biting helical thread formed on the proximal end of the shaft, the thread having a distal face and a proximal face, the distal face of the thread forming an angle of about 72° with respect to a perpendicular to the central axis of the implant, and the proximal face of the thread forming an angle of about 18° with respect to a perpendicular to the central axis of the implant, such that the implant can be driven by impaction into a pre-drilled bone site, and removed from the bone site by rotation.

2. The implant of claim 1, wherein the distal portion of the shaft is tapered.

3. The implant of claim 1, wherein the shaft has a smooth central portion.

4. The implant of claim 1, further comprising an attachment point for a driver.

5. The implant of claim 1, wherein the thread is a continuous, unbroken helix.

6. The implant of claim 1, wherein the thread is rigid.

7. The implant of claim 1, wherein the thread and the implant are machined from a single piece of material.

8. The implant of claim 1, wherein the implant is made of a biologically resorbable material.

* * * * *